United States Patent
Odidi et al.

(10) Patent No.: US 6,509,037 B2
(45) Date of Patent: Jan. 21, 2003

(54) SUSTAINED RELEASE PHARMACEUTICAL MATRIX TABLET OF PHARMACEUTICALLY ACCEPTABLE SALTS OF DICLOFENAC AND PROCESS FOR PREPARATION THEREOF

(76) Inventors: Isa Odidi, 2136 Opal Court, Mississauga, Ontario (CA), L5K 2S5; Amina Odidi, 2136 Opal Court, Mississauga, Ontario (CA), L5K 2S5

(*) Notice: Subject to any disclaimer, the term of this patent is extended or adjusted under 35 U.S.C. 154(b) by 0 days.

(21) Appl. No.: 09/945,056

(22) Filed: Aug. 31, 2001

(65) Prior Publication Data

US 2002/0051817 A1 May 2, 2002

Related U.S. Application Data

(63) Continuation of application No. 09/054,942, filed on Apr. 3, 1998, now Pat. No. 6,312,724.
(60) Provisional application No. 60/036,550, filed on Apr. 4, 1997.

(51) Int. Cl.[7] ............................... A61K 9/16; A61K 9/22
(52) U.S. Cl. ..................... 424/468; 424/486; 424/488; 424/499; 424/501
(58) Field of Search ..................... 424/441, 468–470, 424/474, 994–995, 486, 488, 480, 499, 501; 514/974; 264/331.12

(56) References Cited

U.S. PATENT DOCUMENTS

| | | | |
|---|---|---|---|
| 4,726,951 A | 2/1988 | Panoz et al. | |
| 4,867,985 A | 9/1989 | Heafield et al. | |
| 4,948,581 A | 8/1990 | Sawayanagi et al. | |
| 4,968,505 A | 11/1990 | Okada et al. | |
| 5,215,755 A | * | 6/1993 | Roche et al. |
| 5,639,475 A | | 6/1997 | Bettman et al. |
| 6,312,724 B1 | * | 11/2001 | Odidi et al. |

FOREIGN PATENT DOCUMENTS

| | | |
|---|---|---|
| EP | 383967 | 8/1990 |
| EP | 255002 | 5/1992 |
| EP | 200213 | 7/1992 |
| EP | 365480 | 8/1992 |
| EP | 288138 | 9/1992 |
| EP | 324981 | 3/1993 |
| EP | 386688 | 4/1993 |
| EP | 599767 | 6/1994 |
| JP | 59059632 | 4/1984 |
| JP | 61044811 | 3/1986 |
| JP | 2237918 | 9/1990 |
| JP | 8175983 | 7/1996 |
| WO | WO 94/03160 | 2/1994 |
| WO | WO 97/02017 | 1/1997 |

* cited by examiner

*Primary Examiner*—Edward J. Webman
(74) *Attorney, Agent, or Firm*—Isabelle Clauss; Foley Hoag LLP

(57) ABSTRACT

The present invention provides a novel sustained release composition and method for making such a composition of diclofenac and its pharmaceutically acceptable salts. The composition of the present invention provides a sustained release formulation of diclofenac and pharmaceutically acceptable salts thereof which is suitable for once daily administration and provides controlled and long lasting in vivo release. The composition comprises: (a) about 5–25% by weight of hydroxyethyl cellulose; (b) about 5–75% by weight of lactose; (c) about 0–3% by weight of silicone dioxide; (d) about 0.5–5% by weight of PVP; (e) about <3% by weight of talc; and f) about <3% by weight of magnesium stearate.

9 Claims, No Drawings

SUSTAINED RELEASE PHARMACEUTICAL MATRIX TABLET OF PHARMACEUTICALLY ACCEPTABLE SALTS OF DICLOFENAC AND PROCESS FOR PREPARATION THEREOF

CROSS REFERENCE TO RELATED APPLICATIONS

This application is a continuation of U.S. patent application Ser. No. 09/054,942 filed Apr. 3, 1998, now U.S. Pat. No. 6,312,724, which claims the benefit of U.S. Provisional Application Ser. No. 60/036,550 filed Apr. 4, 1997.

FIELD OF THE INVENTION

The present invention relates to a composition of diclofenac and its pharmaceutically acceptable salts. More particularly, the present invention relates to a sustained release composition of diclofenac and its salts and a method for making such a composition.

BACKGROUND OF THE INVENTION

Diclofenac is a nonsteroidal anti-inflammatory drug (NSAID) which provides anti-inflammatory, analgesic, and antipyretic activity in humans. Salts of diclofenac, benzeneacetic acid derivatives, are designated chemically as 2-[(2,6-dichlorophenyl)amino] benzeneacetic acid salt. A delayed release formulation of diclofenac, Voltaren™ Delayed release, has been developed and utilizes diclofenac sodium salt in an enteric coated tablet which acts to resist the release of diclofenac in the low pH of gastric fluid, however, it allows rapid release of drug in the higher pH of the duodenum.

As understood in the prior art, enteric coatings are not an efficient method for the delivery of NSAIDs such as diclofenac due to the inability of such coating systems to provide or achieve a sustained therapeutic effect due to the lack of prolonged release of the pharmaceutical agent with only a single dose over a long period of time. Enteric coats are designed to dissolve or breakdown in an alkaline environment. The presence of food may increase the pH of the stomach. Therefore, the concurrent administration of enteric coated diclofenac with food or the presence of food in the stomach may lead to dose dumping and unwanted secondary effects. Furthermore, given the fact that NSAIDs can cause stomach irritation and sometimes peptic ulceration and gastrointestinal bleeding, it would be desirable to have a drug delivery system that is capable of providing the controlled delivery of diclofenac or other pharmaceutically acceptable salts of diclofenac in a predictable manner over a long period of time.

SUMMARY OF THE INVENTION

The present invention provides a novel sustained release composition and method for making such a composition of diclofenac and its pharmaceutically acceptable salts.

According to an object of the present invention is a sustained release formulation of diclofenac and pharmaceutically acceptable salts thereof, the composition being suitable for once daily administration and provides controlled and long lasting in vivo release. The composition preferably delivers not more than 10% diclofenac in about 5 hours at an acid pH of about<4.5 and delivers greater than 50% of diclofenac in 12 hrs at a pH of about<6.5 in a controlled manner during in vivo and in vitro dissolution.

According to an object of the present invention is a method for making a controlled sustained release composition of diclofenac and its pharmaceutically acceptable salts, the method comprising intimately blending diclofenac or a pharmaceutically acceptable salt of diclofenac, with a suitable water swellable hydrogel, a channeling agent and binder.

It is another objective of the present invention to provide a sustained release formulation of pharmaceutically acceptable salts of diclofenac in a simple and cost effective manner without the need for expensive special coatings or structures. It is still a further objective of the present invention to provide modified release formulation of diclofenac and pharmaceutically acceptable salts thereof using a non aqueous wet granulation process.

DETAILED DESCRIPTION OF THE PREFERRED EMBODIMENTS

The invention comprises a sustained release composition of diclofenac and pharmaceutically active salts thereof and a process for making such a composition. The composition is preferably provided as a sustained release matrix tablet.

In the preferred method, the sustained release matrix tablet is made in accordance with the following steps:

I) intimately blending a pharmaceutically acceptable salt of diclofenac (about 5–35% by wt) with about 5–25% hydroxyethylcellulose (preferably Natrosol(â) 250HHX PHARM), silicon dioxide (about<2%) and a channeling agent preferably anhydrous lactose (about 20–65%) in a planetary or high shear mixer;

II) granulating the homogeneous blend from step I with about<5% solution of polyvinypyrrolidone (PVP) in isopropyl alcohol in a planetary or high shear mixer. It is preferable to knead the wet mass for 1–3 minutes after wet granulation;

III) drying the wet granules in a fluid bed dryer or tray dryer to a loss on drying (LOD) of about<3%. Preferably the granules are dried in a tray dryer at about>40 degrees centigrade to an LOD of about<2%;

IV) size reducing of the dried granules from step III in a mill preferably Cone mill such that granule size is about<1400 microns;

V) intimately blending the milled granules with a glidant such as talc (<3%) in a V-blender;

VI) intimately blending the talc treated granules with a lubricant such as magnesium stearate (about<3%) in a V-blender; and VII) compressing the lubricated granules from step VI using a rotary tablet press into tablets with an excipient to a pharmaceutically acceptable salt of diclofenac component ratio of about 2:1 to about 3:1. The resulting tablets have a hardness of about 5–20 Strong Cobb units and friability of about<1%.

By providing the optimum combination of excipients such as hydroxyethylcellulose, silicon dioxide and lactose and granulating with a non aqueous solution of PVP in an optimum combination and using the method as described above, the sustained release matrix tablet of diclofenac and pharmaceutically acceptable salts of diclofenac of the present invention is provided. The composition is suitable for once daily administration and is capable of delivering not more than about 10% of diclofenac in 5 hours at acid pH of about<4.5 and delivering greater than about 50% of diclofenac in 12 hrs at a pH of about>6.5 in a controlled and predictable manner in dissolution tests. The present invention provides the unique "pseudo enteric" behaviour as a direct result of the use of enteric and pH sensitive polymers.

Hydroxyethyl cellulose serves to produce an intricate matrix structure in which the active drug substance is homogeneously embedded. The matrix has a network of crosslinks in which there is physical entrapment of the desired pharmaceutically active agent in a hydrogel domain formed when the composition as a matrix tablet absorbs water and swells to form a gelatinous barrier around the tablet core. This provides excellent diffusion controlled drug release in the presence of channeling agents such as lactose. Lactose is water soluble. In the gastrointestinal (GIT) fluid, the tableted composition will dissolve leaving behind channels through which GIT fluid gains access into the tablet matrix causing the pharmaceutically active agent to dissolve and diffuse out. This channelization mechanism is more efficient in ensuring diffusion controlled drug release than is the "wicking" mechanism exhibited by wicking agents such as microcrystalline cellulose. In order for HEC to maintain it's swelling and gelation properties in vivo it is preferred that wet granulation be carried out using a non aqueous solvent such as isopropyl alcohol 99%.

It is understood by those skilled in the art that the sustained release characteristic of the composition can be predetermined and varied by adjusting the makeup of the composition within the aforesaid limits with other excipients known to those skilled in the art. The duration, uniformity and continuity of the release of diclofenac can be suitably controlled by varying the relative amount of hydroxyethylcellulose and lactose. The finished tablet may be optionally film coated.

EXAMPLES

The examples are described for the purposes of illustration and are not intended to limit the scope of the invention.

Methods of synthetic chemistry, pharmacy and pharmacology referred to but not explicitly described in this disclosure and examples are reported in the scientific literature and are well known to those skilled in the art.

Example 1

Diclofenac Sodium ER 100 mg Tablet

|  | % composition | mg per tablet |
|---|---|---|
| Diclofenac sodium | 33.3 | 99.9 |
| Natrosol 250 IFHX | 25 | 75 |
| Lactose | 35.7 | 107.1 |
| Silicone dioxide | 1 |  |
| PVP | 3 | 9 |
| Talc |  |  |
| Magnesium stearate | 1 | 3 |

Example 2

Diclofenac Sodium ER 50 mg Tablet

|  | % composition | mg per tablet |
|---|---|---|
| Diclofenac sodium | 19.2 | 50 |
| Natrosol 250 HHX | 20 | 52 |
| Lactose | 54.8 | 142.5 |
| Silicone dioxide | 1 | 2.6 |
| PVP | 3 | 7.8 |
| Talc | 1 | 2.6 |
| Magnesium stearate | 1 | 2.6 |

Example 3

Diclofenac Sodium ER 75 mg Tablet

|  | % composition | Mg per tablet |
|---|---|---|
| Diclofenac sodium | 25 | 75 |
| Natrosol 250 HHX | 15 | 45 |
| Lactose | 54 | 162 |
| silicone dioxide | 1 | 3 |
| PVP | 3 | 9 |
| Talc | 1 | 3 |
| Magnesium stearate | 1 | 3 |

We claim:

1. A method for making an extended release formulation for diclofenac and pharmaceutically acceptable salts of diclofenac, said method comprising the steps of:
   (i) blending about 5–25% by weight of hydroxyethyl cellulose, about 5–75% by weight of lactose and about 0–3% by weight of silicon dioxide;
   (ii) granulating the blend of (i) with about 0.5–5% by weight of polyvinylpyrrolidone (PVP);
   (iii) milling (ii) and blending with about 1–3% by weight talc; and
   (iv) blending (iii) with about 1–3% by weight magnesium stearate.

2. The method of claim 1, wherein the hydroxyethyl cellulose is Natrosol™ 250OHHR.

3. The method of claim 1, wherein the lactose is anhydrous and directly compressible.

4. The method of claim 1, wherein the method additionally comprises forming (iv) as a tablet.

5. The method of claim 4, wherein said tablet is coated with a pharmaceutically acceptable film coat.

6. The method of claim 4, wherein said tablet is suitable for once daily administration, said tablet delivering not more than about 10% of diclofenac in 5 hours at acid pH of about <4.5 and delivering greater than about 50% of diclofenac in 12 hours at a pH of about >6.5 in vivo and in vitro dissolution tests.

7. The method of claim 1, wherein step (ii) is conducted using a non-aqueous granulating solvent.

8. The method of claim 1, wherein said lactose is replaced or combined with a water soluble pharmaceutical excipient selected from the group consisting of calcium phosphate, calcium sulfate and silicified microcrystalline cellulose.

9. A method for making an extended release formulation for diclofenac and pharmaceutically acceptable salts of diclofenac, said method comprising the steps of:
   (i) blending together about 5–35% by weight diclofenac or a pharmaceutically acceptable salt of diclofenac, about 5–25% by weight of hydroxyethyl cellulose, about 5–75% by weight of lactose and about 0–3% by weight of silicon dioxide;
   (ii) granulating the blend of (I) with about 0.5–5% by weight of polyvinylpyrrolidone (PVP);
   (iii) milling (ii) and blending with about 1–3% by weight talc; and
   (iv) blending (iii) with about 1–3% by weight magnesium stearate.

* * * * *